United States Patent [19]

Foster et al.

[11] Patent Number: 4,668,689
[45] Date of Patent: May 26, 1987

[54] GLUTARIMIDE DERIVATIVES FOR TREATING OESTROGEN-DEPENDENT TUMORS

[75] Inventors: Allan B. Foster, Carshalton Beeches; Michael Jarman, London; Chui-Sheung Kwan, Epsom, all of England

[73] Assignee: National Research Development Corporation, England

[21] Appl. No.: 753,878

[22] Filed: Jul. 11, 1985

[30] Foreign Application Priority Data

Jul. 19, 1984 [GB] United Kingdom ............... 8418422
Dec. 28, 1984 [GB] United Kingdom ............... 8432741

[51] Int. Cl.$^4$ ............... A61K 31/445; C07D 401/04
[52] U.S. Cl. ................................... 514/318; 546/193
[58] Field of Search ..................... 546/193; 514/318

[56] References Cited

U.S. PATENT DOCUMENTS

| | | | |
|---|---|---|---|
| 2,673,205 | 3/1954 | Hoffmann et al. | 546/193 |
| 2,848,455 | 8/1958 | Hoffmann et al. | 546/219 |
| 4,058,573 | 11/1977 | Knell | 570/137 |

FOREIGN PATENT DOCUMENTS

| | | | |
|---|---|---|---|
| 2089883 | 5/1984 | Australia | 546/193 |
| 1013654 | 8/1957 | Fed. Rep. of Germany | 546/194 |
| 8502618 | 6/1985 | World Int. Prop. O. | 546/193 |

OTHER PUBLICATIONS

D. E. Seitz et al., Chemical Abstracts, 95, 115233g, (1981).
B. D. Anderson et al., Chemical Abstracts, 91, 95p, (1979).
J. Knabe et al., Chemical Abstracts, 101, 37882u, (1984).
J. Knabe et al., Arch. Pharm., 317, 614–619, (1984).
I. E. Smith et al., British Medical Journal, 283, 1432–1434, (1981).
A. B. Foster et al., J. Med. Chem. 28, 200–204, (1985).
P. E. Graves et al., Endocrinology, 105, 52–57, (1979).
E. Tagmann et al., Helv. Chim. Acta, 35, 1541, (1952).
K. Hoffmann et al., Helv. Chim. Acta, 46, 387–394, (1957).
S. Kukolja et al., Croatica Chimica Acta, 33, 41–44, (1961).
R. Paul et al., J. Med. Chem., 17, 539–541, (1972).
G. Pifferi et al., J. Med. Chem., 18, 741, (1975).
R. Grigg et al., Tetrahedron Letters, 22, 4107, (1981).
R. Grigg et al., Chemical Communications, 611, (1981).

Primary Examiner—Richard A. Schwartz
Attorney, Agent, or Firm—Jacobs & Jacobs

[57] ABSTRACT

In the treatment of oestrogen-dependent tumors, it is desirable to improve the therapy obtainable from the compound aminoglutethimide. It has now been found that 3-ethyl-3-(4-pyridyl)glutarimide derivatives of formula

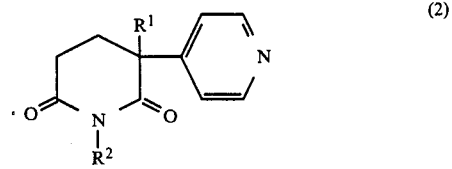

(2)

wherein:
(a) $R^1$ represents an ethyl group and $R^2$ represents a methyl group, an alkyl or cycloalkyl group having 3 to 10 carbon atoms, or a fluoroalkyl group having 2 to 10 carbon atoms;
(b) $R^1$ represents an alkyl group having 3 to 10 carbon atoms or a fluoroalkyl group having 2 to 5 carbon atoms and $R^2$ represents a hydrogen atom; or,
(c) $R^1$ represents an alkyl group having 3 to 8 carbon atoms or a fluoroalkyl group having 2 to 5 carbon atoms and $R^2$ represents an alkyl or fluoroalkyl group having 2 to 8 carbon atoms, provided that the total number of carbon atoms in $R^1$ and $R^2$ is not more than 10;

and therapeutically acceptable acid addition salts of the above compounds.

9 Claims, No Drawings

GLUTARIMIDE DERIVATIVES FOR TREATING OESTROGEN-DEPENDENT TUMORS

BACKGROUND OF THE INVENTION

1. Field of the Invention

This invention relates to derivatives of piperidine-2,6-dione, also known as glutarimide, its preparation and pharmaceutical compositions containing it.

2. Description of the Prior Art

U.S. Pat. No. 2,673,205 (Ciba) claims 3,3-disubstitutedglutarimides of formula

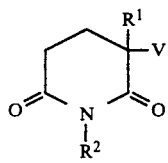

(1)

where $R^1$ represents an aliphatic hydrocarbyl group of 1 to 6 carbon atoms and V represents a phenyl or pyridyl group, and $R^2$ represents hydrogen or a substituent group such as alkyl, acyl, phenyl or benzyl. The class of compounds claimed in U.S. Pat. No. 2,673,205 is stated to have an anti-convulsive effect. However, the preferred compound, 3-ethyl-3-phenylglutarimide was subsequently marketed as the sedative and hypnotic agent glutethimide. The later U.S. Pat. No. 2,848,455 (Ciba) claims 3-methyl and -ethyl-3-(4-aminophenyl)glutarimides as anti-convulsive agents. The 3-ethyl compound is known as aminoglutethimide.

Certain compounds of formula (1) wherein $R^1$ is a straight chain alkyl group of 1 to 4 carbon atoms and V is a phenyl, 1,2-cyclohexenyl or cylcohexyl group are reported to have varying degrees of CNS activity, see J. Knabe et al., Arch. Pharm. 317 614–619 (1984).

The present invention is concerned with an entirely different field of therapy, namely anti-cancer therapy, specifically the treatment of oestrogen-dependent tumours. Such tumours are most commonly produced in the breast tissue of female mammals. Within the last 5 years or so aminoglutethimide has come seriously into the reckoning for treatment of advanced breast cancer in post-menopausal patients. Its advantages over tamoxifen have been set out in a recent paper by I. E. Smith et al., British Medical Journal, 283, 1432–1434 (1981). One important factor in the success of aminoglutethimide in this connection is its ability to inhibit in vivo the activity of the enzyme aromatase in peripheral tissue. This enzyme is required for the conversion of androgens into oestrogens, viz. androstenedione to oestrone and testosterone to oestradiol. Aminogluthethimide therefore breaks the metabolic pathway to oestrogens. Unfortunately, however, aminoglutethimide also inhibits the enzyme desmolase which is required for the metabolic conversion of cholesterol to corticosteroids. Since the body needs corticosteroids, treatment with aminoglutethimide has to be supplemented by cortisone replacement therapy. Furthermore, depletion of corticosteroids causes a reflex rise in adrenocorticotrophic hormone (ACTH) which stimulates the conversion of cholesterol to pregnenolone by the enzyme desmolase and consequently the production of oestrogen precursors.

Recently, it has been found that the compound 3-ethyl-3-(4-pyridyl)glutarimide inhibits aromatase but not desmolase. This finding was surprising in that neither its nearest phenyl analogue, aminoglutethimide, nor its nearest pyridyl analogues, having the pyridine ring N-atom in the 2- or 3-position, showed this property. The finding is the subject of PCT Patent Application GB No. 84/00425 (National Research Development Corporation) designating U.S. and Japan, published 20th June 1985 as WO No. 85/02618 and UK and foreign equivalents thereof, all claiming priority of 9th December 1983. See also A. B. Foster et al., J. Med Chem. 28, 200–204 (1985).

SUMMARY OF THE INVENTION

It has now been found that certain derivatives of 3-ethyl-3-(4-pyridyl)glutarimide, referred to hereinafter as "pyridoglutethimide" for brevity, also inhibit aromatase but not demolase and that many of these derivatives are more powerful aromatase inhibitors than pyridoglutethimide, while still having no marked effect on desmolase. Like pyridoglutethimide, they also have little or no CNS (sedative-hypnotic) activity.

The invention provides glutarimide derivatives which are compounds of the general formula

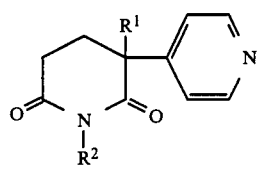

(2)

wherein:

(a) $R^1$ represents an ethyl group and $R^2$ represents a methyl group, an alkyl or cycloalkyl group having 3 to 10 carbon atoms, or a fluoroalkyl group having 2 to 10 carbon atoms;

(b) $R^1$ represents an alkyl group having 3 to 10 carbon atoms or a fluoroalkyl group having 2 to 5 carbon atoms and $R^2$ represents a hydrogen atom; or, (c) $R^1$ represents an alkyl group having 3 to 8 carbon atoms or a fluoroalkyl group having 2 to 5 carbon atoms and $R^2$ represents an alkyl or fluoroalkyl group having 2 to 8 carbon atoms, provided that the total number of carbon atoms in $R^1$ and $R^2$ is not more than 10;

and therapeutically acceptable acid addition salts of the above compounds.

The derivatives of the invention are useful in cancer therapy for the treatment of oestrogen-dependent tumours in mammals, and the invention accordingly also provides the derivatives both per se and for such use.

DESCRIPTION OF THE PREFERRED EMBODIMENTS

The preferred sub-classes of pyridoglutethimide derivatives of the invention are:

"N-alkyl" compounds wherein $R^1$ represents an ethyl group and $R^2$ represents an alkyl group having 5 to 10 carbon atoms or a fluoroalkyl group having 2 to 6 carbon atoms;

"C-alkyl" compounds wherein $R^1$ represents an alkyl group having 3 to 10 carbon atoms or a fluoroalkyl group having 2 to 5 carbon atoms, and $R^2$ represents a hydrogen atom; and "Mixed alkyl" compounds wherein $R^1$ represents an alkyl group having 3 to 6 carbon atoms and $R^2$ an alkyl group having 2 to 5 carbon atoms, and the total number of carbon atoms in $R^1$ and $R^2$ is from 5 to 8.

In the "N-alkyl" type, (a), of derivatives of the invention, $R^1$ was maintained as an ethyl group, as in aminoglutethimide and pyridoglutethimide, while the piperidine ring N-atom was substituted by a substituent $R^2$ which was varied. It was found that when $R^2$ is methyl the aromatase inhibition was not as strong as in pyridoglutethimide ($R^2$=H) and that making $R^2$ ethyl caused it to disappear altogether. Higher alkyl substitution of straight-chain alkyl groups of 3 to 6 carbon atoms produced varying degrees of aromatase inhibition which only reached that of pyridoglutethimide when $R^2$ was n-hexyl. Very surprisingly, however, it was found that when $R^2$ was made n-heptyl, n-octyl or n-nonyl, the aromatase inhibition showed a dramatic increase. Accordingly, the higher alkyl derivatives, in which $R^2$ has 5 to 9 or 10 carbon atoms, whether in a straight or branched chain, are preferable from this point of view. Among the fluoroalkyl compounds those having 4 to 8 carbon atoms are preferred.

$R^2$ can alternatively be cycloalkyl. The term "cycloalkyl" is used herein to include groups consisting of simply a cycloalkane ring residue, groups in which the cycloalkane ring residue is substituted by an alkyl group as in 4-methylcyclohexyl, for example, and groups which are alkyl groups substituted by a cycloalkane ring residue, as in cyclohexylmethyl, for example. Thus "cycloalkyl" includes groups which could be defined alternatively as alkylcycloalkyl and (cycloalkyl)alkyl. Preferably the open-chain alkyl group is methyl and cycloalkyl group has from 5 to 7 carbon atoms.

In the "C-alkyl" type, (b), of derivatives of the invention, $R^2$ was maintained as a hydrogen atom, as in aminoglutethimide and pyridoglutethimide, while $R^1$ was varied. The $R^1$=methyl derivative was a very poor aromatase inhibitor, but it was surprisingly found that the straigh-chain higher alkyl derivatives were excellent aromatase inhibitors, better than pyridoglutethimide, and that the degree of inhibition improved as the higher alkyl series was ascended to 9 carbon atoms. Accordingly preferred compounds of the invention are those in which $R^1$ has 3 to 9 carbon atoms. $R^1$ can, of course, have a straight or branched chain. Suitably, $R^1$ may also be fluoroalkyl having 3 to 5 carbon atoms.

In the "mixed alkyls" of type (c), aromatase inhibition is again high, but falls off as the total number of carbon atoms in $R^1$ and $R^2$ increases. At 16 such total carbon atoms or above aromatase inhibition ceases. It has also been found that the compound in which $R^1$ is n-octyl and $R^2$ is n-butyl shows no aromatase inhibition and that the compound in which $R^1$ is n-octyl and $R^2$ is n-hexyl shows significant desmolase inhibition.

There are some preliminary indications that the longer chain non-fluorinated compounds might be more readily metabolised and accordingly compounds at the lower ends of the preferred ranges in all types of derivative do have more merit than might otherwise appear.

Fluorination of the alkyl group appears to bring about high aromatase inhibition equivalent to that obtained with unsubstituted alkyl derivatives having longer alkyl chains. The preferred fluorine derivatives are those in which the end carbon atom, remote from the piperidine ring, in the chain is fluorinated, most preferably trifluorinated. Desirably the $R^1$ and/or $R^2$ group is of formula —$(CH_2)_n(CF_2)_mCF_3$ wherein n and m are 0 or integers, n being preferably from 1 to 4 and m being preferably 0 or an integer, the total number of carbon atoms in the group being dictated by any of the values of $R^1$ and $R^2$ defined above. Most desirably n=2. The fluoroalkyl groups like the alkyl groups, are not necessarily straight-chained.

All the derivatives of the invention are optically active. The invention includes them in the form of their individual optical isomers and mixtures thereof, especially racemates. The R isomer [cf. the R isomer of aminoglutethimide, P. E. Graves et al., Endocrinology, 105, 52–57 (1979)] is expected to show the greater inhibition of aromatase.

The type (b) derivatives of the invention (those wherein $R^1$ represents an alkyl group and $R^2$ represents a hydrogen atom) can be prepared by a process which comprises reacting a compound of formula:

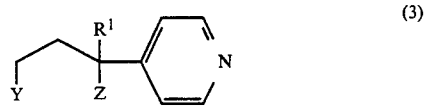

(3)

wherein $R^1$ is as defined above, each of Y and Z independently represents a carboxylic acid group or a ring closing, reactable derivative group thereof or a precursor of such an acid or derivative group and at least one of Y and Z represents an amide group or precursor thereof, under conditions effective to bring about ring closure between the amide group and the said carboxylic acid or derivative group thereof (which might or might not also be an amide group), whereby a piperidine-2,6-dione ring is formed.

Thus, one of Y and Z is conveniently an amide group or a cyano (CN) group. The cyano group is a precursor of the amide group, being convertible thereinto by the action of strong mineral acid, and the conditions required will normally include providing the strong mineral acid and preferably also heating. The other one of Y and Z can also be amide or cyano, in which case the conditions will of course include provision for hydrolysis of the amide. Where the other one of Y and Z is a carboxylic acid group or a non-amide derivative thereof, e.g. an ester, preferably a methyl or ethyl ester, heat will normally be required to effect the ring closure. Other reactive derivative groups such as acid chloride or azide, for example, will also be usable under appropriate conditions. Many analogous such ring closure reactions have been described e.g. by E. Tagmann et al., Helv. Chim. Acta 35, 1541 (1952), K. Hoffman et al., ib id., 46, 387 (1957), U.S. Pat. Nos. 2,673,205 and 2,848,455, S. Kukolja et al., Croatica Chimica Acta 33, 41 (1961), R. Paul et al., J. Med. Chem., 17, 539 (1972) and G. Pifferi et al., J. Med. Chem. 18, 741 (1975). Appropriate conditions can therefore be deduced by those skilled in the art.

A preferred procedure of the present invention comprises heating a 4-cyano-4-(4-pyridyl)alkanonitrile of formula (3) wherein Y and Z both represent cyano groups, with a strong mineral acid, e.g. sulphuric and/or hydrochloric acid, so as to bring about amide formation and thereafter ring-closing the amide under hydrolysis conditions and separating the desired 3-alkyl-3-(4-pyridyl)glutarimide from the reaction mixture.

The starting dinitrile, a 4-cyano-4-(4-pyridyl)alkanonitrile, can be prepared by reacting a 2-(4-pyridyl)alkanonitrile with acrylonitrile. The mononitriles of formula (4)

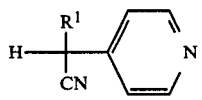
(4)

can be prepared in various ways. For example they can be prepared by reaction of 4-pyridylacetonitrile with an alkali, followed by an alkyl iodide or bromide. Alkylation can sometimes occur at both hydrogens of the alpha-carbon atom, leading to the unwanted, dialkylated compound, a 2-alkyl-2-(4-pyridyl)alkanonitrile. This can be separated, e.g. by chromatography, or the mixture thereof with the desired, monoalkylated compound, the 2-(4-pyridyl)alkanonitrile of formula (4) can be subjected to the reaction with acetonitrile and ring-closure as described above and the unwanted by-product separated at the end of the synthesis.

A method of preparing 2-(4-pyridyl)alkanontriles of formula (4) in which $R^1$ represents a straight chain alkyl group having up to 7 carbon atoms comprises heating 4-pyridylacetonitrile with a primary alcohol, a trivalent rhodium salt and triphenylphosphine under mildly alkaline conditions, e.g. using an alkali metal carbonate. This reaction gives specifically the monoalkylated derivatives desired, substantially free of unwanted dialkyl derivatives. The reaction is known for 4-phenylacetonitrile from R. Grigg et al., Tetrahedron Letters 22, 4107 (1981) and Chemical Communications 611 (1981). The use of an alkyl bromide, chloride or iodide or a fluoroalkyl iodide together with caesium carbonate, in place of the alcohol/triphenyl phosphine and alkali metal carbonate is suggested for the preparation when R' has any of the other defined meanings.

The type (a) and (c) derivatives of the invention, (those wherein $R^2$ represents an alkyl or cycloalkyl group) can be prepared by an appropriate N-alkylation of the piperidine ring N-atom of pyridoglutethimide or the appropriate 3-alkyl derivative thereof. Thus, heating pyridoglutethimide or a 3-alkyl derivative thereof, respectively, with an alkyl bromide or iodide or a fluoroalkyl iodide and caesium carbonate yielded the desired N-alkyl or -fluoroalkyl derivatives in good yield.

Acid addition salts, e.g. the phosphate or hydrochloride, can be prepared by conventional methods.

The glutarimide derivatives of the invention are normally prepared in racemic form and the optical isomers can be resolved, if desired, by conventional methods, for example by preparation and separation of tartrate salts and re-liberation of the optically active free base. Alternatively the dinitrile precursor, i.e. 4-cyano-4-(4-pyridyl)hexanonitrile, can be resolved into its optical isomers and the ring-closing preparative reaction carried out on the desired isomer to yield the corresponding optical isomer of the glutarimide product. The 1-alkyl-3-alkyl-3-(4-pyridyl)glutarimides of the invention when prepared as described above have the same stereochemistry as the starting 3-alkyl-3-(4-pyridyl)-glutarimides from which they were prepared.

The present invention also provides a pharmaceutical composition which comprises a therapeutically effective amount of a glutarimide derivative of the invention, in association with a therapeutically acceptable carrier or diluent. The composition of the invention can, for example, be in a form suitable for parenteral (e.g. intravenous, intramuscular or intracavitary), oral, topical or rectal administration. Particular forms of the composition may be, for example, solutions, suspensions, emulsions, creams, tablets, capsules, liposomes or micro-reservoirs, especially compositions in orally ingestible or sterile injectable form. The preferred form of composition contemplated is the dry solid form, which includes capsules, granules, tablets, pills, boluses and powders. The solid carrier may comprise one or more excipients, e.g. lactose, fillers, disintegrating agents, binders, e.g. cellulose, carboxymethylcellulose or starch or anti-stick agents, e.g. magnesium stearate, to prevent tablets from adhering to tabletting equipment. Tablets, pills and boluses may be formed so as to disintegrate rapidly or to provide slow release of the active ingredient.

The present invention also includes a method of treating oestrogen-dependent tumours in the mammalian body which comprises administering a glutarimide derivative of the invention to a mammalian patient in a therapeutically effective dose, e.g. in the range 0.025-0.25 mmole/kg body weight, preferably 0.025-0.1 mmole/kg, administered daily during the course of the treatment.

In addition to its use as a single agent, a glutarimide derivative of the invention could be co-administered with, administered in sequence with, or contained in a mixed formulation with other compatible agents effective against tumours of the kind described, e.g. aminoglutethimide, tamoxifen or danazol. It can also be used as a component of a combined modality treatment, for example including radiotherapy and/or surgery.

The following Examples illustrate the invention. All temperatures are in degrees Celsius.

EXAMPLE 1

Preparation of 3-ethyl-3-(4-pyridyl)piperidine-2,6-dione

4-Pyridylacetonitrile (5.6 g, 47.46 mmol) dissolved in ethanol (70 ml) was heated under reflux with rhodium chloride trihydrate (624 mg, 2.37 mmol), triphenylphosphine (3.11 g, 11.87 mmol) and anhydrous sodium carbonate (5.534 g, 52.2 mmol) for 20 hours, filtered and concentrated. Elution from a column (4.5, 35 cm) of silica gel (Merck 7734) with $CHCl_3$ afforded a pure fraction of 2-(4-pyridyl)butyronitrile (5.44 g, 78.5% yield). This was taken up in t-butanol (15 ml) and stirred with 'Triton B' (0.2 ml) and acrylonitrile (2.5 ml, 58 mmol) for 2 hours. Excess solvent was evaporated and the residue was diluted with water (200 ml). Extraction from $CHCl_3$ (2×100 ml) afforded impure 2-ethyl-2-(4-pyridyl)butyronitrile which was heated under reflux with a mixture of glacial acetic acid (30 ml) and concentrated sulphuric acid (6 ml) for 3 hours and poured onto ice water. Sodium hydrogen carbonate was added to neutralise the solution, to pH 7-7.5 and the solution was then extracted with $CHCl_3$. Column chromatography (3×20 cm, silica gel, $CHCl_3$:MeOH 19:1 v/v) of the crude product afforded a pure fraction of the title compound, (3.29 g), in a 40.2% yield based on 2-(4-pyridyl)-butyronitrile. The title compound was crystallised from toluene, m.p. 138–139° (corrected).

EXAMPLE 2

Preparation of other 3-alkyl-3-(4-pyridyl)piperidine-2,6-diones

Using the procedures of Example 1 and other normal primary alcohols (n-propyl, n-butyl, n-pentyl, n-hexyl, n-heptyl) in place of ethanol, the analogous 3-n-propyl, n-butyl, n-pentyl, n-hexyl and n-heptyl derivatives were prepared. Their physical and analytical data are shown in Table 1 below.

EXAMPLE 3

4-Pyridylacetonitrile (1.18 g, 0.01 mole) dissolved in acetonitrile (20 ml) was heated under reflux with n-octyl bromide (1.73 ml, 0.01 mole) and caesium carbonate (4 g) for 1 hour, filtered and concentrated. Elution from a column of silica gel as described in Example 1 gave 2-(4-pyridyl)decanonitrile (1.58 g, 69% yield).

EXAMPLE 4

Using the procedure of Example 3 and n-nonyl bromide instead of n-octyl bromide, the analogous 3-n-nonyl derivative was prepared. Its physical and analytical data are shown in Table 1.

EXAMPLE 5

Using the procedure of Example 3 and fluoroalkyl iodides $I(CH_2)_2CF_3$ (prepared as described below), $I(CH_2)_2CF_2CF_3$ and $I(CH_2)_2(CF_2)_2CF_3$ (prepared according to the procedure of U.S. Pat. No. 4,058,573), but in the second and third-mentioned cases changing the solvent to propionitrile instead of acetonitrile, the analogous 3-(3,3,3-trifluoropropyl), (3,3,4,4,4-pentafluorobutyl) and (3,3,4,4,5,5,5-heptafluoropentyl) derivatives were prepared. These derivatives were identified by the mass spectroscopy of the $(M+1)^+$ molecular ion, the masses having the predicted value in each case.

1-Iodo-3,3,3-trifluoropropane was prepared as follows.

A mixture of ethylene (16.9 g) and trifluoromethyl iodide (12.6 g) was kept in a stainless steel pressure vessel at 270° and 88.5 atmospheres (maximum for 5 hours. The resulting liquid (13.7 g) contained a mixture having as major components $CF_3CH_2CH_2I$ and $CF_3(CH_2CH_2)_2I$. Fractional distillation of such mixtures, to which toluene had been added, gave 1-iodo-3,3,3-trifluoropropane, $CF_3CH_2CH_2I$, b.p. 90°, containing a trace of toluene.

(b) $R^2 = -CH_2CF_3$, $-CH_2(CF_2)_2CF_3$; X=I for 0.5 hours, and the reaction product was filtered and the filtrate concentrated. (The above fluoroalkyl iodides are available commercially or were prepared according to the procedure of U.S. Pat. No. 4,058,573.) Column chromatography (3×15 cm; silica gel, CHCl₃) of the filtrate afforded nearly quantitative yields (which ranged from 90 to 95%) of the appropriate N-alkyl derivative, in each case as an oil. The products were identified by mass spectroscopy of the $(M+1)^+$ molecular ion, the masses having the predicted values in each case.

EXAMPLE 7

Preparation of 1,3-dialkyl-3-(4-pyridyl)piperidine-2,6-diones

Following the procedure of Example 3, 3-alkyl-3-(4-pyridyl)-piperidine-2,6-diones in which the 3-alkyl group is n-butyl, and n-hexyl were N-alkylated by heating under reflux with $Cs_2CO_3$ and n-butyl and ethyl bromide respectively again in acetonitrile, and the products worked up in a similar way, and identified by mass spectroscopy.

Biochemical Tests

The activities of the glutarimide derivatives of the invention against the enzymes aromatase and desmolase were assayed as follows. Each test compound was examined over a range of concentrations. At each concentration of the test compound, samples were removed at three time points. The results were plotted on a graph of amount of product released against time of incubation. The resulting graph was used to determine the activity of the enzyme in terms of the rate of enzyme reaction at each concentration of the test compound. The values were compared with control samples (no test compound present) run simultaneously.

The results were expressed as $IC_{50}$ values, which is the concentration of inhibitor required to reduce the activity of the enzyme to 50% of its control value at the

TABLE 1

| Compound (3-alkyl group) | m.p. (°C.) | Required % C | H | N | Formula | Found % C | H | N | m.p. (°C.) | Molecular Ion[b] (M + 1)+ |
|---|---|---|---|---|---|---|---|---|---|---|
| Methyl | 156-7[c] | 47.12 | 3.49 | 16.16 | $C_{17}H_{15}N_5O_9$ | 46.91 | 3.61 | 15.83 | 160 (dec) | 205 |
| n-Propyl | 150-1[c] | 49.46 | 4.15 | 15.18 | $C_{19}H_{19}N_5O_9$ | 49.65 | 4.20 | 15.34 | 210 (dec) | 233 |
| n-Butyl | 130-1[c] | 50.42 | 4.45 | 14.73 | $C_{20}H_{21}N_5O_9$ | 50.43 | 4.57 | 14.90 | 158 (dec) | 247 |
| n-Pentyl | 115-6[c] | 51.53 | 4.74 | 14.31 | $C_{21}H_{23}N_5O_9$ | 51.31 | 4.77 | 14.50 | 85 (dec) | 261 |
| n-Hexyl | 106.5[d]-107.5 | 52.48 | 5.01 | 13.91 | $C_{22}H_{25}N_5O_9$ | 52.24 | 4.98 | 14.03 | 158 (dec) | 275 |
| n-Heptyl | oil | 53.38 | 5.26 | 13.54 | $C_{23}H_{27}N_5O_9$ | 53.33 | 5.36 | 13.72 | 91 (dec) | 289 |
| n-Octyl | oil | 55.74 | 5.38 | 12.89 | $C_{24}H_{29}N_5O_9$ | 54.98 | 5.57 | 13.06 | 95 (dec) | 303 |
| n-Nonyl | oil | 55.04 | 5.73 | 12.84 | $C_{25}H_{31}N_5O_9$ | 55.19 | 5.96 | 12.83 | 89 (dec) | 317 |

[a]All picrates were crystallised from ethanol.
[b]Molecular ion determination by mass spectroscopy was done in methane chemical ionisation.
[c]Crystallised from toluene.
[d]This compound solidified.

EXAMPLE 6

Preparation of 1-alkyl-3-ethyl-3-(4-pyridyl)piperidine-2,6-diones

3-Ethyl-3-(4-pyridyl)piperidine-2,6-dione (218 mg, 1 mmol) dissolved in (a) acetonitrile or (b) propionitrile (5 ml) was heated under reflux with $Cs_2CO_3$, $R^2$ X (2 mmol, (a) $R^2$=n-propyl, isopropyl, butyl, isobutyl, n-pentyl, 2-methylbutyl(S), n-hexyl, cyclohexylmethyl, n-heptyl, n-octyl, n-nonyl and n-decyl; X=Br and $R^2 = -(CH_2)_2CF_3$, $-(CH_2)_2(CF_2)_3CF_3$, $-(CH_2)_2(CF_2)_5CF_3$ and $-(CH_2)_2(CF_2)_7CF_3$; X=I and substrate concentration employed, namely 1.5 micromolar (³H) testosterone or 0.38 micromolar (³H) androstene-3,17-dione for the aromatase enzyme and 7 micromolar (¹⁴C) cholesterol for the desmolase enzyme. The two aromatase tests have different significances. Inhibition of both oeshone and oestradiol is believed to be important in the therapy of oestrogen-dependent breast tumours. Since there is evidence that oestradiol (produced from testosterone in vivo) might be a more important factor than oestrone (produced from androstenedione in vivo) in hormone-dependent breast cancers, the testosterone test is particularly relevant.

A. Desmolase The mitochondrial fraction of bovine adrenal cortex provided the source of desmolase and the method of isolation was essentially as published by R. B. Hochberg et al., Biochemistry, 13, 603 (1974). The enzyme activity was assayed using (26-$^{14}$C)-cholesterol as substrate and measuring the $^{14}$C-isocaproic acid released, see R. B. Hochberg et al., supra, and V. I. Uzgiris et al., Endocrinology, 101, 89 (1977). Inhibitor compounds were added in ethanol (10 microliters) and an equal volume of ethanol was added to the control assay. The total volume of the assay mixture was 1.0 ml. After preincubating the assay tubes at 30° C. for 5 minutes, the reaction was started by the addition of 1 mg of mitochondrial protein. Samples were removed after 2,4 and 6 minutes of incubation and the assay completed as described.

B. Aromatase Aromatase was obtained from the microsomal fraction of human placental tissue, as described by K. J. Ryan, J. Biol. Chem. 234, 268 (1959). Activity was monitored by measuring the $^3H_2O$ formed from (1,2-$^3$H) testosterone or during (1,2-$^3$H) androstene-3,17-dione during aromatization, see P. E. Graves et al., Endocrinology, 105, 52 (1979). The assay procedure was as described above, except that after preincubation of the tubes at 30° C. for 5 minutes the reaction was started by the addition of 0.5 mg of microsomal protein. Samples were taken after 5, 10 and 15 minutes of incubation.

Results are shown in Table 3 below. "None" indicates that there was no inhibition. "Comp." refers to a comparative result relating to a compound not within the invention, viz aminoglutethimide and various compounds of formula (2) but with other meanings of $R^1$ and $R^2$.

TABLE 3

Inhibitory power of pyridoglutethimide and derivatives thereof versus aromatase and desmolase

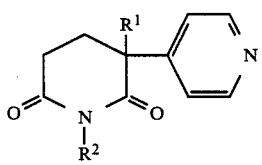

(2)

| Compound | | IC$_{50}$, micromolar concentrations | | |
|---|---|---|---|---|
| | | Aromatase | | Desmolase |
| $R_1$ | $R_2$ | Testosterone | Androstenedione | |
| Aminoglutethimide (Comp.) | | 8 | 14 | 30 |
| Pyridoglutethimide (Comp.) | | 10 | 45 | none |
| $C_2H_5$ | H | | | |
| $C_2H_5$ | H (Comp.) | 10 | | none |
| $C_2H_5$ | $CH_3$ | 30 | | none |
| $C_2H_5$ | n-$C_2H_5$ (Comp.) | 28 | | 92 |
| $C_2H_5$ | n-$C_3H_7$ | 31 | | none |
| $C_2H_5$ | n-$C_4H_9$ | 40 | | none |
| $C_2H_5$ | n-$C_5H_{11}$ | 21 | | 209 |
| $C_2H_5$ | n-$C_6H_{13}$ | 7 | | none |
| $C_2H_5$ | n-$C_7H_{15}$ | 1.5 | | 210 |
| $C_2H_5$ | n-$C_8H_{17}$ | 0.8 | 5 | 110 |
| $C_2H_5$ | n-$C_9H_{19}$ | 3.0 | | 175 |
| $C_2H_5$ | n-$C_{10}H_{21}$ | 10 | | 340 |
| $C_2H_5$ | —CH$_2$—cyclohexyl | 9 | | none |

TABLE 3-continued

Inhibitory power of pyridoglutethimide and derivatives thereof versus aromatase and desmolase

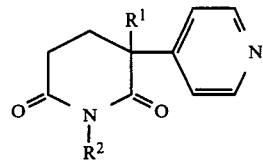

(2)

| Compound | | IC$_{50}$, micromolar concentrations | | |
|---|---|---|---|---|
| | | Aromatase | | Desmolase |
| $R_1$ | $R_2$ | Testosterone | Androstenedione | |
| $C_2H_5$ | $CH_2CF_3$ | 14 | 31 | >350 |
| $C_2H_5$ | $CH_2CH_2CF_3$ | 11 | 42 | none |
| $C_2H_5$ | $CH_2(CF_2)_2CF_3$ | 19 | 106 | none |
| $C_2H_5$ | $(CH_2)_2(CF_2)_2CF_3$ | 3.0 | 15 | 240 |
| $C_2H_5$ | $(CH_2)_2(CF_2)_3CF_3$ | 9 | 9 | 120 |
| $C_2H_5$ | $(CH_2)_2(CF_2)_5CF_3$ | 34 | 23 | 145 |
| $C_2H_5$ | $(CH_2)_2(CF_2)_7CF_3$ | 15 | none | 150 |
| H | H (Comp.) | >105 | none | |
| $CH_3$ | H (Comp.) | 245 | | none |
| $C_2H_5$ | H | 10 | | none |
| n-$C_3H_7$ | H | 6 | | none |
| n-$C_4H_9$ | H | 4 | | none |
| n-$C_5H_{11}$ | H | 3.2 | | none |
| n-$C_6H_{13}$ | H | 3.8 | | none |
| n-$C_7H_{15}$ | H | 2.0 | | none |
| n-$C_8H_{17}$ | H | 0.3 | 0.6 | none |
| n-$C_9H_{19}$ | H | 2.4 | | none |
| $(CH_2)_2CF_3$ | H | 2.9 | 7 | none |
| $(CH_2)_2(CF_2)_2CF_3$ | H | 18 | 22 | none |
| $(CH_2)_2(CF_2)_3CF_3$ | H (Comp.) | 18 | 22 | none |
| $(CH_2)_2(CF_2)_5CF_3$ | H (Comp.) | none | none | 93 |
| $(CH_2)_2(CF_2)_7CF_3$ | H (Comp.) | | none | 79 |
| $CH_3$ | $CH_3$ (Comp.) | >90 | | none |
| n-$C_4H_9$ | n-$C_4H_9$ | 2.1 | | none |
| n-$C_6H_{13}$ | n-$C_2H_5$ | 2.1 | | none |
| n-$C_8H_{17}$ | n-$C_4H_9$ | none | | 106 |
| n-$C_8H_{17}$ | n-$C_6H_{13}$ | 10 | | 73 |
| n-$C_8H_{17}$ | n-$C_8H_{17}$ | none | | 169 |

We claim:

1. A compound of the formula

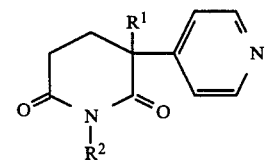

(2)

wherein:

(a) $R^1$ represents an ethyl group and $R^2$ represents a methyl group, an alkyl or cycloalkyl group having 3 to 10 carbon atoms, or a fluoroalkyl group having 2 to 10 carbon atoms;

(b) $R^1$ represents an alkyl group having 3 to 10 carbon atoms or a fluoroalkyl group having 2 to 5 carbon atoms and $R^2$ represents a hydrogen atom; or, (c) $R^1$ represents an alkyl group having 3 to 8 carbon atoms or a fluoroalkyl group having 2 to 5 carbon atoms and $R^2$ represents an alkyl or fluoroalkyl group having 2 to 8 carbon atoms, provided that the total number of carbon atoms in $R^1$ and $R^2$ is not more than 10;

or a therapeutically acceptable acid addition salt thereof.

2. The compound according to claim 1, wherein $R^1$ represents an ethyl group and $R^2$ represents an alkyl group having from 5 to 10 carbon atoms or a fluoroalkyl group having 2 to 6 carbon atoms.

3. The compound according to claim 1, wherein $R^1$ represents an alkyl group having 3 to 9 carbon atoms or a fluoroalkyl group having 3 to 5 carbon atoms and $R^2$ represents a hydrogen atom.

4. The compound according to claim 1, wherein $R^1$ represents an alkyl group having 3 to 6 carbon atoms and $R^2$ an alkyl group having 2 to 5 carbon atoms and the total number of carbon atoms in $R^1$ and $R^2$ is from 5 to 8.

5. The compound according to claim 1, wherein the $R^2$ alkyl group is a primary alkyl group.

6. The compound according to claim 1, wherein $R^2$ is a fluoroalkyl group of the formula $-(CH_2)_2(CF_2)_mCF_3$, wherein m is an integer of from 0 to 7.

7. The compound according to claim 1, wherein $R^1$ is a fluoralkyl group of the formula $-(CH_2)_2(CF_2)_mCF_3$, wherein m is an integer of from 0 to 2.

8. A pharmaceutical composition for the treatment of oestrogen-dependent tumors in mammals, comprising a therapeutically effective amount of the compound claimed in claim 1, in association with a therapeutically acceptable carrier or diluent.

9. A method of treating a mammal suffering from an oestrogen-dependent tumor, which comprises administering to the sufferer a therapeutically effective amount of the compound according to claim 1.

* * * * *